(12) United States Patent
Renault et al.

(10) Patent No.: US 8,492,445 B2
(45) Date of Patent: Jul. 23, 2013

(54) EMULSIFYING COMPOSITIONS BASED ON ALKYL POLYGLYCOSIDES AND ESTERS

(75) Inventors: Benjamin Renault, Lyons (FR); Boris Estrine, Nanteuil la Foret (FR); Charles Portella, Cormontreuil (FR); Cedric Ernenwein, Nouvion le Vineux (FR); Fabien Massicot, Warmeriville (FR); Sinisa Marinkovic, Avancon (FR)

(73) Assignees: Bioamber SAS, Pomacle (FR); Universite de Reims Champagne Ardenne (U.R.C.A.), Reims Cedex (FR); Centre National de Recherche Scientifique (C.N.R.S.), Paris Cedex (FR)

( * ) Notice: Subject to any disclaimer, the term of this patent is extended or adjusted under 35 U.S.C. 154(b) by 555 days.

(21) Appl. No.: 12/717,231

(22) Filed: Mar. 4, 2010

(65) Prior Publication Data
US 2010/0234320 A1      Sep. 16, 2010

(30) Foreign Application Priority Data
Mar. 11, 2009   (FR) ..................... 09 01124

(51) Int. Cl.
*B01F 17/56*  (2006.01)
*B01F 17/00*  (2006.01)
*A61K 8/06*   (2006.01)
*A61K 8/18*   (2006.01)
*A61K 8/34*   (2006.01)
*A61K 8/37*   (2006.01)
*A61K 8/60*   (2006.01)
*A61Q 19/00*  (2006.01)

(52) U.S. Cl.
USPC ............. 516/73; 516/75; 516/204; 516/918; 424/401; 424/47; 424/58; 424/59; 424/69; 424/70.13; 424/70.22; 514/25; 514/939; 510/470

(58) Field of Classification Search
USPC ............. 516/74, 73, 75, 204, 918; 424/401, 424/47, 58, 59, 69, 70.13, 70.22; 514/25, 514/939; 510/470
See application file for complete search history.

(56) References Cited

U.S. PATENT DOCUMENTS

| | | | | |
|---|---|---|---|---|
| 4,195,177 | A * | 3/1980 | Inoue et al. | 536/18.2 |
| 4,305,961 | A * | 12/1981 | Tsutsumi et al. | 514/939 |
| 4,309,447 | A * | 1/1982 | Tsutsumi et al. | 514/939 |
| 4,396,520 | A * | 8/1983 | Payne et al. | 510/470 |
| 4,806,275 | A * | 2/1989 | Johnson et al. | 510/535 |
| 5,756,072 | A * | 5/1998 | Beck et al. | 424/49 |
| 5,795,978 | A * | 8/1998 | Ansmann et al. | 536/120 |
| 6,162,423 | A * | 12/2000 | Sebag et al. | 424/70.12 |
| 6,245,821 | B1 | 6/2001 | Bulcourt et al. | |
| 6,569,410 | B1 * | 5/2003 | Fabry et al. | 424/59 |
| 6,596,779 | B1 * | 7/2003 | Jean-Noel et al. | 516/72 |
| 7,335,627 | B1 * | 2/2008 | O'Lenick et al. | 424/70.13 |
| 7,871,766 | B2 * | 1/2011 | Pauly et al. | 435/6.16 |
| 2001/0008935 | A1 | 7/2001 | Milius et al. | |
| 2002/0187167 | A1 * | 12/2002 | Vacher et al. | 424/401 |
| 2005/0069512 | A1 | 3/2005 | Roso et al. | |
| 2005/0136081 | A1 | 6/2005 | Kawa et al. | |
| 2005/0226824 | A1 * | 10/2005 | Kawa et al. | 424/59 |
| 2006/0078568 | A1 * | 4/2006 | Pauly et al. | 424/195.16 |
| 2007/0122370 | A1 * | 5/2007 | Behler et al. | 424/70.13 |
| 2007/0128232 | A1 * | 6/2007 | Rahse | 424/401 |

FOREIGN PATENT DOCUMENTS

| | | | |
|---|---|---|---|
| DE | 19542572 A1 | | 5/1997 |
| FR | 2913896 A | * | 9/2008 |
| WO | 2005110588 A | | 11/2005 |
| WO | 2005121294 A | | 12/2005 |
| WO | 2008135646 A1 | | 11/2008 |

OTHER PUBLICATIONS

S.N. Zlatanos et al, "A New Method of Synthesis of Alkyl-Glycidyl Esters of Dicarboxylic Acids in High Yields", JAOCS, vol. 67, No. 10 (Oct. 1990), pp. 661-664.*

Machine translation of WO 2005/101588 A1, Decription pp. 1-35, online @ http://worldwide.espacenet.com/publicationDetails/description?CC=WO&NR=2005110588A1&KC=A1&FT=D&ND=3&date=20051124&DB=EPODOC&locale=en_EP, (downloaded Jun. 9, 2012), pp. 1-17.*

Machine translation of FR 2913896 A1, Decription pp. 1-35, online @ http://worldwide.espacenet.com/, (downloaded Jun. 9, 2012), pp. 1-11.*

French Search Report dated Nov. 13, 2009, French Patent Application No. 09 01124, filed Mar. 11, 2009.

* cited by examiner

*Primary Examiner* — Daniel S Metzmaier
(74) *Attorney, Agent, or Firm* — Pearne & Gordon LLP

(57) ABSTRACT

An emulsifying composition, characterised in that it contains by weight, excluding impurities, (i) 1 to 98% by weight of a mixture of alkyl glycosides $R1O(G1)g_1(G2)g_2(G3)g_3(G4)g_4(G5)g_5$, (ii) 1 to 90% by weight of a mixture of alcohol esters $R2OZ$, (iii) 1 to 90% of an alcohol $R3OH$, and (iv) 4 to 90% of a mixture of alkyl glycoside esters $R4O(X1)x_1(Z)z_1(X2)x_2(Z)z_2(X3)x_3(Z)z_3(X4)x_4(Z)z_4(X5)x_5(Z)z_5$, is disclosed In accordance with the composition, R1 is a hydrocarbon radical, linear or branched, saturated or unsaturated, having 10 to 22 carbon atoms. G1, G2, G3, G4, G5 are identical or different residues of -oses selected from glucose, galactose, mannose, fructose, ribose, xylose and arabinose, $g_1, g_2, g_3, g_4$ and $g_5$ being equal to 0 or 1, the sum of $g_1, g_2, g_3, g_4$ and $g_5$ being at least equal to 1. The composition has emulsifying capacity in the presence of electrolytes or in the case of paraffin-based emulsions.

14 Claims, No Drawings

EMULSIFYING COMPOSITIONS BASED ON ALKYL POLYGLYCOSIDES AND ESTERS

The present invention provides novel emulsifying compositions based on alkyl polyglycosides (APGs) and derivatives of succinic acid. Surprisingly these compositions have improved emulsifying properties.

A second aspect of the invention relates to a product for topical use containing the novel composition.

APGs are non-ionic surfactant compounds derived from reducing sugars such as glucose, fructose, mannose, galactose, arabinose, xylose, lyxose, ribose. Their method of acquisition and their use are widely described in the prior art, for example in patents U.S. Pat. Nos. 3,598,865, 3,721,633, 3,772,269. These compounds are conventionally obtained by a glycosylation reaction using one or more alcohols with one or more reducing sugars. APGs are mixtures of molecules characterised firstly by the nature of the alcohol or the blend of alcohols used to build the alkyl chain and secondly by their average degree of polymerisation, in other words the average number of units of reducing sugars grafted by alcohol. APGs can have an average degree of polymerisation of between 1.1 and 5. They can be used on their own or in conjunction with other surfactants in a wide range of industrial applications. The properties sought by users are substantially dependent on the area of application. The advantages of APGs are their biodegradability and their acceptable ecotoxicity profile. These advantages mean that this family of surfactants is very widely used in formulations for cosmetic, domestic or industrial use.

APGs are used in particular as an emulsifying agent in the preparation of continuous aqueous or oil phase emulsions, mini-emulsions or micro-emulsions (U.S. Pat. No. 6,596,779, WO 2005110588). Emulsions are found in cosmetics, pharmaceuticals or dermopharmaceuticals (milks, creams, ointments). In the cosmetics and pharmaceutical sectors, for the development of hygiene or personal care products, emulsions are an effective means of obtaining a harmonious combination of ingredients of differing nature and properties in a homogeneous and easy-to-use form.

In these sectors APGs do not always allow the formulation of emulsions which are sufficiently stable over time (WO 92/06778, WO 95/13863, WO/9822207). These emulsions are also known not to tolerate the presence of electrolytes. Finally, in the case of paraffin-based emulsions, it is sometimes very difficult to obtain continuous aqueous phase emulsions with an acceptable viscosity, in other words with a viscosity of less than 60,000 centipoise, with APGs as the emulsifying system. In order to compensate for this drawback, the formulator will combine the emulsifying system with additives such as polymers, complexing agents or hydrotropes, which are expensive and difficult to use.

There is therefore a need for surfactant compositions whose emulsifying capacity is improved in comparison to prior art compositions, in particular in the presence of electrolytes or in the case of paraffin-based emulsions.

The object underlying the present invention relates first of all to novel emulsifying compositions which allow the various problems and disadvantages associated with prior art APG-based compositions to be avoided. These surfactant compositions are free from coupling agents and hydrotropes and from ethylene or propylene oxide derivatives and from compounds derived from environmentally hazardous amines.

The compositions according to the present invention have improved surfactant properties in comparison to the prior art, are easy to handle and can therefore be used in a wide range of applications, including personal care products.

During the course of its investigations, the applicant found that compositions containing both APGs and esters of the fatty alcohol succinate type and optionally the alkyl polypentoside succinate type whose alkyl chains contain 10 to 22 carbon atoms had surfactant properties which had hitherto been unsuspected.

The compositions according to the present invention are characterised in that they contain by weight, excluding impurities:

1 to 98% and preferably 5 to 95% by weight of a mixture of alkyl glycosides of formula (1)

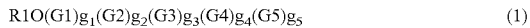
$$R1O(G1)g_1(G2)g_2(G3)g_3(G4)g_4(G5)g_5 \quad (1)$$

in which:
R1 is a hydrocarbon radical, linear or branched, saturated or unsaturated, having 10 to 22 carbon atoms,
G1, G2, G3, G4, G5 are identical or different residues of -oses selected from glucose, galactose, mannose, fructose, ribose, xylose and arabinose
$g_1, g_2, g_3, g_4$ and $g_5$ being equal to 0 or 1, the sum of $g_1, g_2, g_3, g_4$ and $g_5$ being at least equal to 1

1 to 90% and preferably 5 to 75% by weight of a mixture of alcohol esters of formula (2)

$$R2OZ \quad (2)$$

in which:
R2 is a hydrocarbon radical, linear or branched, saturated or unsaturated, having 2 to 22 carbon atoms, which can optionally be identical to R1
Z is then a radical of formula $-(CO)(CH2)_2(CO)OM$ obtained by esterification of succinic acid by R2OH in which M is H, Na, K, $NH_4$, $[HO(CH2)2]3NH$, R2

1 to 90% and preferably 4 to 80% of an alcohol of formula (3),

$$R3OH \quad (3)$$

in which:
R3 is a hydrocarbon radical, linear or branched, saturated or unsaturated, having 10 to 22 carbon atoms, which can optionally be identical to R1 and/or R2

0 to 97% and preferably 4 to 90% of a mixture of alkyl glycoside esters of formula (4)

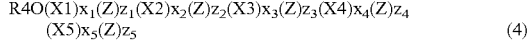
$$R4O(X1)x_1(Z)z_1(X2)x_2(Z)z_2(X3)x_3(Z)z_3(X4)x_4(Z)z_4(X5)x_5(Z)z_5 \quad (4)$$

in which:
R4 is a hydrocarbon radical, linear or branched, saturated or unsaturated, having 10 to 22 carbon atoms, which can optionally be identical to R1 and/or R2 and/or R3
X1, X2, X3, X4, X5 are identical or different residues of -oses selected from ribose, xylose and arabinose
$x_1, x_2, x_3, x_4$ and $x_5$ being equal to 0 or 1, the sum of $x_1, x_2, x_3, x_4$ and $x_5$ being at least equal to 1
Z is then a radical of formula $-(CO)(CH2)_2(CO)OM$ obtained by esterification of succinic acid by a free hydroxyl of X1, X2, X3, X4 or X5, in which M is H, Na, K, $NH_4$, $[HO(CH2)2]3NH$, R1, R2, R3, R4
$z_1, z_2, z_3, z_4, z_5$ being equal to 0, 1, 2, 3 or 4, the sum of $z_1, z_2, z_3, z_4, z_5$ being at least equal to 1.

In the context of an economic implementation of the invention, blends of alcohols which are commercially available and consist of 2 or 3 different alcohols are used to synthesise the various constituents of the compositions.

Thus R1, R2, R3 and R4 are preferably selected from alkyl residues obtained from linear primary alcohols deriving from vegetable oils, namely the radicals 2-ethyl-decyl, n-dodecyl, 2-ethyl-dodecyl, n-tetradecyl, 2-ethyl-tetradecyl, n-hexadecyl, 2-ethyl-hexadecyl, n-octadecyl, 2-ethyl-octadecyl, behenyl or arachidyl.

The alkyl polyglycosides of formula (1) described above can be synthesised by the numerous methods of organic chemistry known to date.

For example, a conventional route used for the preparation of alkyl polyglycosides is an acetalisation reaction. This method involves bringing into contact one or more reducing sugars and one or more alcohols in the presence of an acid catalyst, at a temperature of between 50 and 140° C. for a period of 15 minutes to 6 hours, and eliminating water from the reaction medium until a solution of alkyl polyglycosides is obtained, and optionally separating the alkyl polyglycosides from this solution.

The acid catalyst used is preferably sulfuric acid, a sulfonic acid such as methanesulfonic acid, hydrochloric acid, hypophosphorous acid or any other acid catalyst allowing the reaction to be performed.

The reaction is preferably performed in the complete absence of solvents, but if necessary a solvent such as an oxide ether, such as tetrahydrofuran, diethyl oxide, 1,4-dioxane, isopropyl oxide, methyl tert-butyl ether, ethyl tert-butyl ether or diglyme, a halogenated hydrocarbon or a solvent of the amide family such as N,N-dimethyl formamide, an alkane such as hexane or an aromatic solvent such as toluene can be used.

If present, the reaction solvent can be eliminated in order to collect the mixture of alkyl polyglycosides. The acid catalyst can then be neutralised and the solution filtered. The neutralisation is performed for example by means of a hydrogen carbonate or an alkali or alkaline-earth carbonate, in particular sodium hydrogen carbonate, by means of an alkali or alkaline-earth hydroxide, in particular sodium hydroxide, or by means of an organic base such as triethanolamine.

The alkyl polyglycosides can then be purified either by evaporation of the excess alcohols under vacuum of between 0.1 and 100 mbar at a temperature of between 60 and 200° C., preferably using a film evaporator, or by chromatography on a silica gel, aluminium oxide or activated carbon column or on an ion-exchange resin, or by crystallisation in a solvent.

The alkyl polyglycosides can if necessary be decolourised by adding 0.05 to 10%, preferably 0.5 to 3%, of hydrogen peroxide, alkali or alkaline-earth peroxodisulfates, perborates, persulfates, perphosphates, percarbonates, ozone or periodates at a temperature of between 15 and 100° C. 30 or 50% hydrogen peroxide is preferred.

The alkyl polyglycosides can be prepared from pure or mixed sugar sources. The use of alkyl polyglycosides obtained from syrups of reducing sugars derived from high-hemicellulose plant raw materials or from products or co-products of agricultural origin, such as products or co-products of maize (bran, fibres and husks of maize), barley (bran) or co-products of wheat (bran and straw) or co-products of wood containing pentoses is preferred.

The compounds of formula (2) and (4) described above can be synthesised by the numerous methods of organic chemistry known to date. One route which is conventionally used for example is an esterification reaction.

In our case this method involves bringing into contact succinic acid or a derivative or salts thereof and,
in the case of compounds of formula (2), one or more alcohols of formula R2OH,
in the case of compounds of formula (4), one or more glycosides of formula $R4O(X1)x_1(X2)x_2(X3)x_3(X4)x_4(X5)x_5$
optionally in the presence of an acid or basic catalyst at a temperature of between 50 and 240° C. for a period of 15 minutes to 6 hours and optionally eliminating water from the reaction medium until a solution of compounds of formula (2) and/or (4) is obtained.

The preparation of compounds of formula (2) and (4) can be carried out in a single esterification reaction. In this case succinic acid or a derivative thereof is reacted with at least one compound R2OH and at least one glycoside of formula $R4O(X1)x_1(X2)x_2(X3)x_3(X4)x_4(X5)x_5$.

Of the derivatives or salts of succinic acid, succinic anhydride, diethyl succinate, dibutyl succinate and diammonium succinate are preferably used.

If a basic catalyst is used, a hydrogen carbonate or an alkali or alkaline-earth carbonate, in particular potassium carbonate, or an alkali or alkaline-earth hydroxide, in particular sodium hydroxide, potassium hydroxide or an organic base such as triethanolamine is preferably used.

If an acid catalyst is used, sulfuric acid, a sulfonic acid such as methanesulfonic acid, hydrochloric acid, hypophosphorous acid or any other acid catalyst allowing the reaction to be performed is preferably used.

The reaction is preferably performed in the complete absence of solvents, but if necessary a solvent such as an oxide ether, such as tetrahydrofuran, diethyl oxide, 1,4-dioxane, isopropyl oxide, methyl tert-butyl ether, ethyl tert-butyl ether or diglyme, a halogenated hydrocarbon or a solvent of the amide family such as N,N-dimethyl formamide, an alkane such as hexane or an aromatic solvent such as toluene can be used.

If present, the reaction solvent can be eliminated in order to collect the mixture of compounds of formula (2) and/or (4). The catalyst can then be neutralised and the solution filtered. The compounds of formula (2) and/or (4) can then be purified either by evaporation of the excess alcohols under vacuum of between 0.1 and 100 mbar at a temperature of between 60 and 200° C., preferably using a film evaporator, or by chromatography on a silica gel, aluminium oxide or activated carbon column or on an ion-exchange resin, or by crystallisation in a solvent.

The compositions of the invention likewise have remarkable emulsifying properties, in particular in the presence of electrolytes. An emulsion is a dispersion of a liquid in another immiscible liquid. The compositions of the invention allow stable emulsions to be obtained even when using less than 5% by weight of the emulsifying composition relative to the total weight of the emulsion and even when the emulsion contains more than 0.3% by weight of electrolytes relative to the total weight of emulsion. The stable emulsions thus obtained contain neither polymers nor chelating agents.

The emulsifying capacity of the compositions according to the invention is assessed using the method described in standard NF T 73409. This method involves preparing emulsions, which can contain increasing proportions of salt (NaCl), by mixing at 70° C. 1 to 4% by weight of emulsifying composition relative to the total weight of the emulsion, 15 to 18% by weight of oil relative to the total weight of the emulsion and 81% by weight of demineralised water relative to the total weight of the emulsion. The emulsions are produced by stirring vigorously (8000 rpm) using a mechanical agitator for one minute. They are then allowed to rest for 15 hours at 20° C. The emulsions are judged to be stable if a phase separation of less than 5% is observed relative to the total volume of the emulsion after centrifuging at 4000G for 30 minutes, corresponding to a volume of residual emulsion of 95%.

The viscosity of the emulsions thus obtained does not exceed 100,000 centipoise, preferably 60,000 centipoise. The viscosity of the emulsions is measured at 20° C. using a Brookfield DTDV II viscometer fitted with a no. 63 cylinder at a speed of 12 rpm.

A final aspect of the invention relates to products for topical use containing the compositions according to the invention and intended for the cosmetic and pharmaceutical or dermopharmaceutical markets. Such a product contains at least 0.1% by weight, relative to its total weight, of a composition according to the invention. It may comprise 10-25% by weight of an oil and/or 20-90% by weight of an electrolyte.

The following examples illustrate the invention without limiting its scope:

EXAMPLE 1

Preparation of Compositions According to the Invention

The compositions according to the invention are prepared by mixing varying quantities of a composition A based on alkyl polyglycosides and a composition B of alkyl monosuccinate.

Composition A is obtained by glycosylation of a mixture of hexadecanol and octadecanol by D-xylose in accordance with the protocol of example 4 of patent U.S. Pat. No. 6,596,779.

Composition B is obtained by esterification of a mixture of hexadecanol and octadecanol by succinic anhydride in accordance with a modified protocol of S. N. Zlatanos and A. N. Sagredos (J. Am. Oil Chem. Soc. 67 (1990) 661-664).

| Compositions A | wt. % |
|---|---|
| XYL C16 | 11 |
| XYL C18 | 25 |
| ROH C16 | 12.4 |
| ROH C18 | 31 |
| Impurities and other polyglycosides | sufficient to make 100 |

XYL C16 corresponds to hexadecyl xylosides or to compounds of formula (1) where R1 is a hexadecyl radical, G1 is the xylose residue, a is equal to 1 and b, c, d and e are equal to 0. XYL C18 corresponds to octadecyl xylosides or to compounds of formula (1) where R1 is an octadecyl radical, G1 is the xylose residue, a is equal to 1 and b, c, d and e are equal to 0.
ROH C16 corresponds to hexadecanol or to the compound of formula (3) where R3 is equal to the hexadecyl radical.
ROH C18 corresponds to octadecanol or to the compound of formula (3) where R3 is equal to the octadecyl radical.

| Compositions B | wt. % |
|---|---|
| SuC16Na | 32.5 |
| SuC18Na | 50 |
| ROH C16 | 1.5 |
| ROH C18 | 3.5 |
| Impurities | sufficient to make 100 |

SuC16Na corresponds to sodium hexadecyl succinate or to a compound of formula (2) where R2 is a hexadecyl radical, Z is the succinic acid residue and M is Na.
SuC18Na corresponds to sodium octadecyl succinate or to a compound of formula (2) where R2 is an octadecyl radical, Z is the succinic acid residue and M is Na.
Description of Compositions 1 to 3 According to the Invention

| Composition | wt. % of composition A | wt. % of composition B |
|---|---|---|
| 1 | 90 | 10 |
| 2 | 85 | 15 |
| 3 | 80 | 20 |

EXAMPLE 2

Emulsifying Properties of Compositions 1 to 3 According to the Invention with Paraffin Oil An emulsion is prepared by mixing at 70° C. 0.8 g of emulsifying composition, 4 g of paraffin (Markol 82, marketed by ESSO) and 15.2 g of water purified by reverse osmosis. The emulsion is produced by stirring vigorously (8000 rpm) using a mechanical agitator for one minute. It is then allowed to rest for 15 hours at 20° C. The stability of the emulsion is assessed by determining the volume of residual emulsion relative to the total volume after centrifuging at 4000 G for 30 minutes.

One gram of emulsion is likewise diluted in 20 g of water to check that the emulsion is indeed a continuous aqueous phase emulsion.
Finally the viscosity of the emulsion is measured.

| Composition | % of residual emulsion | Continuous aqueous phase | Viscosity (centipoise) |
|---|---|---|---|
| A | 100 | NO | >100,000 |
| 1 | 95.5 | YES | 18,765 |
| 2 | 100 | YES | 29,054 |
| 3 | 95.5 | YES | 22,047 |
| B | 60 | YES | 2703 |

The compositions according to the invention allow continuous aqueous phase emulsions of an acceptable viscosity (<60,000 centipoise) to be obtained. These emulsions are more than 95% stable.

By contrast, it is noted that compositions A and B do not allow emulsions to be obtained which are simultaneously continuous aqueous phase emulsions, stable and of an acceptable viscosity.

EXAMPLE 3

Emulsifying Properties of Compositions 1 to 3 According to the Invention in the Presence of Electrolyte An emulsion is prepared by mixing at 70° C. 0.8 g of emulsifying composition, 4 g of fatty acid triglycerides (Miglyol 812N marketed by Hüls) and 15.2 g of saline solution of a concentration equal to 50 mmol/l of NaCl. The emulsion is produced by stirring vigorously (8000 rpm) using a mechanical agitator for one minute. It is then allowed to rest for 15 hours at 20° C. The stability of the emulsion is assessed by determining the volume of residual emulsion relative to the total volume after centrifuging at 4000 G for 30 minutes.

One gram of emulsion is likewise diluted in 20 g of water to check that the emulsion is indeed a continuous aqueous phase emulsion.
Finally the viscosity of the emulsion is measured.

| Composition | % of residual emulsion | Continuous aqueous phase | Viscosity (Pa·s) |
|---|---|---|---|
| A | 70 | NO | >100,000 |
| 1 | 100 | YES | 9432 |
| 2 | 100 | YES | 8615 |
| 3 | 100 | YES | 7355 |
| B | 40 | YES | 3617 |

The compositions according to the invention allow continuous aqueous phase emulsions of an acceptable viscosity (<60,000 centipoise) to be obtained. These emulsions are perfectly stable.

By contrast, it is noted that compositions A and B do not allow emulsions to be obtained in the presence of electrolyte which are simultaneously continuous aqueous phase emulsions, stable and of an acceptable viscosity.

EXAMPLE 4

Example of the Preparation of Compositions Based on Glucosides and Succinic Acid Esters Compositions are prepared by mixing varying quantities of a composition (EMULGADE PL 68/50 marketed by COG- NIS or MONTANOV 68 EC marketed by SEPPIC) based on alkyl polyglucosides and fatty alcohols and composition B of alkyl monosuccinate.

Description of Compositions 3 to 6 According to the Invention

| Composition | wt. % of EMULGADE PL 68 | wt. % of composition B |
|---|---|---|
| 4 | 90 | 10 |
| 5 | 85 | 15 |
| 6 | 80 | 20 |

Description of Compositions 7 to 9 According to the Invention

| Composition | wt. % of MONTANOV 68 EC | wt. % of composition B |
|---|---|---|
| 7 | 90 | 10 |
| 8 | 85 | 15 |
| 9 | 80 | 20 |

EXAMPLE 5

Emulsifying Properties of Compositions 4 to 9 in the Presence of Electrolyte

An emulsion is prepared by mixing at 70° C. 0.8 g of emulsifying composition, 4 g of isopropyl myristate (RADIA 7729 marketed by OLEON) and 15.2 g of saline solution of a concentration equal to 50 mmol/l of NaCl. The emulsion is produced by stirring vigorously (8000 rpm) using a mechanical agitator for one minute. It is then allowed to rest for 15 hours at 20° C. The stability of the emulsion is assessed by determining the volume of residual emulsion relative to the total volume after centrifuging at 4000 G for 30 minutes.

One gram of emulsion is likewise diluted in 20 g of water to check that the emulsion is indeed a continuous aqueous phase emulsion.

Finally the viscosity of the emulsion is measured.

| Composition | % of residual emulsion | Continuous aqueous phase | Viscosity (centipoise) |
|---|---|---|---|
| EMULGADE PL 68 | 55 | YES | 14,800 |
| MONTANOV 68 EC | 33 | YES | 8713 |
| 4 | 100 | NO | >100,000 |
| 5 | 90 | YES | 28,683 |
| 6 | 100 | NO | >100,000 |
| 7 | 80 | YES | 12,500 |
| 8 | 74 | YES | 8293 |
| 9 | 95 | YES | 8103 |
| B | 90 | YES | 1687 |

It is noted that the compositions based on alkyl polyglucosides do not produce emulsions which are simultaneously stable, continuous aqueous phase emulsions and of an acceptable viscosity.

EXAMPLE 6

Preparation of Compositions According to the Invention

Several compositions according to the invention are prepared by esterification of a composition C obtained according to example 4 of patent U.S. Pat. No. 6,596,779 with succinic anhydride.

| Compositions C | wt. % |
|---|---|
| XYL C16 | 9.6 |
| XYL C18 | 27.3 |
| ROH C16 | 11 |
| ROH C18 | 34.3 |
| Impurities and other polyglycosides | sufficient to make 100 |

Compositions according to the invention are prepared by placing 100 g of composition C in a glass reactor at 110° C. whilst stirring; 3 to 30 g of succinic anhydride are added and the medium is held at 110° C. whilst stirring for 1 hour.

The compositions according to the invention obtained by this method are described in the table below:

Description of Compositions 10 to 16 According to the Invention

| Composition according to the invention | Quantity of succinic anhydride used (g) | wt. % XYLC16 | wt. % XYLC18 | wt. % SuC16Na | wt. % SuC18Na | wt. % ROHC16 | wt. % ROHC18 | wt. % SuXYLC16 | wt. % SuXYLC18 |
|---|---|---|---|---|---|---|---|---|---|
| 10 | 3 | 8.5 | 22.6 | 0.9 | 3.3 | 9.8 | 27.8 | 0.8 | 3.9 |
| 11 | 6 | 8 | 20.9 | 1 | 4.8 | 9.1 | 29.5 | 1.2 | 2.7 |
| 12 | 9 | 6.2 | 18.2 | 2.5 | 6.6 | 8.6 | 28.5 | 1.4 | 2.7 |
| 13 | 12 | 5.2 | 14.7 | 3.3 | 9.6 | 7.3 | 22.5 | 2.5 | 8 |
| 14 | 15 | 6.3 | 13 | 2.1 | 13.8 | 6.7 | 21.4 | 2.9 | 8.4 |
| 15 | 21 | 3.3 | 9.8 | 4.7 | 12.9 | 5 | 16.6 | 4.1 | 11.9 |
| 16 | 30 | 2.5 | 5.2 | 4.9 | 15.8 | 3.1 | 10 | 5.4 | 16.4 |

For each composition the additional weight to make it up to 100% consists of impurities, succinic acid and polyglycosides.

SuXylC16 corresponds to hexadecyl xyloside succinate or a compound of formula (4) where R4 is a hexadecyl radical, X1 is the xylose residue, X1 is equal to 1, x2, x3, x4 and x5 are equal to 0.

SuXylC18 corresponds to octadecyl xyloside succinate or a compound of formula (4) where R4 is an octadecyl radical, X1 is the xylose residue, X1 is equal to 1, x2, x3, x4 and x5 are equal to 0.

EXAMPLE 7

Emulsifying Properties of Compositions 10 to 16 According to the Invention with Paraffin Oil and Isopropyl Myristate An emulsion is prepared by mixing at 70° C. 0.8 g of emulsifying composition, 4 g of oil (MARKOL 82 paraffin from ESSO and RADIA 7729 isopropyl myristate (IPM) from OLEON) and 15.2 g of water purified by ion exchange. The emulsion is produced by stirring vigorously (8000 rpm) using a mechanical agitator for one minute. It is then allowed to rest for 15 hours at 20° C. The stability of the emulsion is assessed by determining the volume of residual emulsion relative to the total volume after centrifuging at 4000 G for 30 minutes.

One gram of emulsion is likewise diluted in 20 g of water to check that the emulsion is indeed a continuous aqueous phase emulsion.

Finally the viscosity of the emulsion is measured.

| Composition | Oil | % of residual emulsion | Continuous aqueous phase | Viscosity (centipoise) |
|---|---|---|---|---|
| C | Paraffin | 88 | NO | >100,000 |
| 10 | Paraffin | >99 | YES | 25,633 |
| 11 | Paraffin | >99 | YES | 12,347 |
| 12 | Paraffin | 99 | YES | 14,437 |
| 13 | Paraffin | 100 | YES | 13,800 |
| 14 | Paraffin | 100 | YES | 11,391 |
| 15 | Paraffin | 100 | YES | 9431 |
| 16 | Paraffin | 100 | YES | 6301 |
| C | IPM | 75 | YES | 29,233 |
| 10 | IPM | 100 | YES | 21,584 |
| 11 | IPM | >99 | YES | 17,705 |
| 12 | IPM | >99 | YES | 10,493 |
| 13 | IPM | 100 | YES | 11,867 |
| 14 | IPM | 100 | YES | 2942 |
| 15 | IPM | 100 | YES | 2109 |
| 16 | IPM | 100 | YES | 3697 |

Irrespective of the oil, the compositions according to the invention allow stable continuous aqueous phase emulsions of an acceptable viscosity (<60,000 centipoise) to be obtained.

By contrast, composition C does not produce a continuous aqueous phase emulsion of an acceptable viscosity which is stable with paraffin. Moreover, said composition C does not allow an emulsion to be obtained which is stable with IPM.

EXAMPLE 8

Emulsifying Properties of Compositions 10 to 16 According to the Invention in the Presence of Electrolyte An emulsion is prepared by mixing at 70° C. 0.8 g of emulsifying composition, 4 g of oil (Miglyol 812N fatty acid triglycerides marketed by Hüls and RADIA 7729 isopropyl myristate (IPM) from OLEON) and 15.2 g of saline solution of a concentration equal to 50 mmol/l of NaCl. The emulsion is produced by stirring vigorously (8000 rpm) using a mechanical agitator for one minute. It is then allowed to rest for 15 hours at 20° C. The stability of the emulsion is assessed by determining the volume of residual emulsion relative to the total volume after centrifuging at 4000 G for 30 minutes.

One gram of emulsion is likewise diluted in 20 g of water to check that the emulsion is indeed a continuous aqueous phase emulsion.

Finally the viscosity of the emulsion is measured.

| Composition | Oil | % of residual emulsion | Continuous aqueous phase | Viscosity (centipoise) |
|---|---|---|---|---|
| C | Miglyol | 69 | NO | >100,000 |
| 10 | Miglyol | >99 | YES | 15,179 |
| 11 | Miglyol | >99 | YES | 12,549 |
| 12 | Miglyol | 99 | YES | 11,737 |
| 13 | Miglyol | 100 | YES | 3283 |
| 14 | Miglyol | 100 | YES | 5220 |
| 15 | Miglyol | 100 | YES | 1054 |
| 16 | Miglyol | 100 | YES | 2044 |
| C | IPM | <50 | NO | — |
| 10 | IPM | 88 | YES | 3284 |
| 13 | IPM | 100 | YES | 5410 |
| 14 | IPM | 100 | YES | 3000 |

In the majority of cases, irrespective of the oil, the compositions according to the invention allow stable continuous aqueous phase emulsions of an acceptable viscosity (<60,000 centipoise) to be obtained in the presence of electrolyte.

This tolerance to electrolytes is not observed in emulsions produced with composition C.

EXAMPLE 9

Preparation of a Composition According to the Invention and Emulsifying Properties A composition 17 according to the invention is prepared by mixing 100 g of composition 14 with 94 g of hexadecanol and 94 g of octadecanol.

| Composition according to the invention | wt. % XYLC16 | wt. % XYLC18 | wt. % SuC16Na | wt. % SuC18Na | wt. % ROHC16 | wt. % ROHC18 | wt. % SuXYLC16 | wt. % SuXYLC18 |
|---|---|---|---|---|---|---|---|---|
| 17 | 5.25 | 2.2 | 4.6 | 0.74 | 37.4 | 35 | 7.5 | 1 |

The additional weight to make it up to 100% consists of impurities, succinic acid and polyglycosides.

Emulsions are then prepared by mixing at 70° C. 0.8 g of emulsifying composition 17, 4 g of oil (Markol 82 paraffin from ESSO, RADIA 7729 isopropyl myristate (IPM) and RADIA 7732 isopropyl palmitate (IPP) from OLEON) and 15.2 g of water purified by ion exchange. The emulsion is produced by stirring vigorously (8000 rpm) using a mechanical agitator for one minute. It is then allowed to rest for 15 hours at 20° C. The stability of the emulsion is assessed by determining the volume of residual emulsion relative to the total volume after centrifuging at 4000 G for 30 minutes.

One gram of emulsion is likewise diluted in 20 g of water to check that the emulsion is indeed a continuous aqueous phase emulsion.

Finally the viscosity of the emulsion is measured.

| Oil | % of residual emulsion | Continuous aqueous phase | Viscosity (centipoise) |
|---|---|---|---|
| Paraffin | >99 | YES | 35,133 |
| IPM | >99 | YES | 19,200 |
| IPP | 99 | YES | 21,600 |

EXAMPLE 10

Preparation of a Composition According to the Invention

A composition according to the invention is prepared by reacting 413 g of a mixture of hexadecanol and octadecanol (RADIANOL 1769 marketed by OLEON), 150 g of D-xylose and 4.5 g of concentrated sulfuric acid in a stirred glass reactor at 90° C. under 50 mbar. The reaction medium is stirred for 2 hours, then 65 g of succinic acid (marketed by BIOAMBER) are added. The medium is then stirred for a further 2 hours at 90° C. and under 50 mbar. The mixture is then neutralised with an aqueous solution of sodium hydroxide. A composition 18 is obtained.

| Composition according to the invention | wt. % XYLC16 | wt. % XYLC18 | wt. % SuC16 | wt. % SuC18 | wt. % ROHC16 | wt. % ROHC18 | wt. % SuXYLC16 | wt. % SuXYLC18 |
|---|---|---|---|---|---|---|---|---|
| 18 | 2.5 | 7.3 | 4.8 | 15.8 | 4.6 | 16.1 | 6 | 20 |

The additional weight to make it up to 100% consists of impurities, succinic acid and polyglycosides.

SuC16 corresponds to compounds of formula (2) where R2 is a hexadecyl radical, Z is the succinic acid residue and M is Na or R2.

SuC18 corresponds to compounds of formula (2) where R2 is an octadecyl radical, Z is the succinic acid residue and M is Na or R2.

EXAMPLE 11

Preparation of a Cosmetic Cream from a Composition According to the Invention 3 g of composition 17 from example 9 are placed in suspension in 47 g of water purified by reverse osmosis. The mixture is heated to 50° C. and then stirred (500 rpm) for 2 minutes. The emulsion thus formed is then cooled to ambient temperature. This emulsion remains stable for 3 months in an oven at 45° C.

EXAMPLE 12

Preparation of a Self-Tanning Moisturising Cream from a Composition According to the Invention

| | | |
|---|---|---|
| A | Composition 10 from example 6 | 4.0% |
| | Aloe vera | 1.0% |
| | Shea butter | 0.2% |
| | Dimethicone (Brentag) | 2.0% |
| | 2-Octyldodecyl myristate (MOD) | 3.0% |
| | Propyl glycol stearate (Stepan PGMS) | 1.0% |
| | Stearic acid | 1.0% |
| | Vitamin E | 0.1% |
| | Hyaluronic acid (VITALHYAL) | 1.0% |
| B | Glycerol | 10% |
| | Water | sufficient to make 100% |
| C | Dihydroxyacetone | 5.0% |
| | Water | 10.0% |
| D | Fragrance | sufficient quantity |

Method of Preparing the Cream:
all the ingredients from A. Weigh all the ingredients from B and homogenise. Heat separately to 75° C. Stir A with a mechanical stirrer at 800 rpm. Add B to A in a thin stream. Mix at 1300 rpm for a few minutes at 75° C. Allow to cool to 40° C. whilst stirring at 300 rpm. Prepare solution C at ambient temperature. Add C and D to the emulsion. Adjust the pH if necessary.

EXAMPLE 13

Preparation of a Preservative-Free Moisturising Milk from a Composition According to the Invention

| | |
|---|---|
| Composition 12 from example 6 | 2.0% |
| Miglyol 812 N (Hüls) | 3.0% |
| Isostearyl isostearate | 3.0% |
| Dimethicone (Brentag) | 2.0% |
| Stearic acid | 1.0% |
| Hyaluronic acid (VITALHYAL) | 1.0% |
| Water | sufficient to make 100% |

Method of Preparing the Milk:
Weigh all the ingredients. Heat to 75° C. Mix with a mechanical stirrer at 3000 rpm for a few minutes at 75° C. Allow to cool to 30° C. whilst stirring at 500 rpm. Adjust the pH if necessary.

EXAMPLE 14

Preparation of a Preservative-Free Nutritive Hair Balm from a Composition According to the Invention

| | |
|---|---|
| Composition 11 from example 6 | 3.0% |
| Dimethicone (Brentag) | 1.0% |
| Wheat oil | 0.5% |
| Wheat peptides | 0.5% |
| Perfume | sufficient quantity |
| Water | sufficient to make 100% |

Method of Preparation:
Weigh all ingredients apart from the perfume. Heat to 75° C. Stir with a mechanical stirrer at 1300 rpm for 1 minute. Allow to cool to 25° C. whilst stirring at 300 rpm. Add the perfume.

The invention claimed is:

1. A cosmetic, pharmaceutical or dermopharmaceutical product comprising an emulsifying composition and an electrolyte, wherein the emulsifying composition is characterised in that it contains by weight; excluding impurities:
   1 to 98% by weight of a mixture of alkyl glycosides of formula (1)

$$R1O(G1)g_1(G2)g_2(G3)g_3(G4)g_4(G5)g_5 \qquad (1)$$

in which:
   R1 is a hydrocarbon radical, linear or branched, saturated or unsaturated, having 10 to 22 carbon atoms,
   G1, G2, G3, G4, G5 are identical or different residues of -oses selected from glucose, galactose, mannose, fructose, ribose, xylose and arabinose
   $g_1, g_2, g_3, g_4$ and $g_5$ being equal to 0 or 1, the sum of $g_1, g_2, g_3, g_4$ and $g_5$ being at least equal to 1
   1 to 90% by weight of a mixture of alcohol esters of formula (2)

$$R2OZ \qquad (2)$$

in which:
   R2 is a hydrocarbon radical, linear or branched, saturated or unsaturated, having 4 to 22 carbon atoms, which can optionally be identical to R1
   Z is then a radical of formula —(CO)(CH2)$_2$(CO)OM obtained by esterification of succinic acid by R2OH in which M is H, Na, K, NH$_4$, [HO(CH2)2]3NH, R2
   1 to 90% by weight of an alcohol of formula (3), $$R3OH \qquad (3)$$

in which:
   R3 is a hydrocarbon radical, linear or branched, saturated or unsaturated, having 10 to 22 carbon atoms, which can optionally be identical to R1 and/or R2
   and 4 to 90% by weight of a mixture of alkyl glycoside esters of formula (4)

$$R4O(X1)x_1(Z)z_1(X2)x_2(Z)z_2(X3)x_3(Z)z_3(X4)x_4(Z)z_4(X5)x_5(Z)z_5 \qquad (4)$$

in which:
   R4 is a hydrocarbon radical, linear or branched, saturated or unsaturated, having 10 to 22 carbon atoms, which can optionally be identical to R1, R2 or R3
   X1, X2, X3, X4, X5 are identical or different residues of oses selected from ribose, xylose and arabinose
   $x_1, x_2, x_3, x_4$ and $x_5$ being equal to 0 or 1, the sum of $x_1, x_2, x_3, x_4$ and $x_5$ being at least equal to 1
   Z is then a radical of formula —(CO)(CH2)$_2$(CO)OM obtained by esterification of succinic acid by a free hydroxyl of X1, X2, X3, X4 or X5, in which M is H, Na, K, NH$_4$, [HO(CH2)2]3NH, R1, R2, R3, R4
   $z_1, z_2, z_3, z_4, z_5$ being equal to 0, 1, 2, 3 or 4, the sum of $z_1, z_2, z_3, z_4, z_5$ being at least equal to 1;
   wherein said product is characterised in that it contains at least 0.1% by weight, relative to the total weight of the product, of the emulsifying composition;
further wherein said product comprises 10 to 25% by weight of a paraffin oil.

2. The product according to claim 1, characterised in that the alkyl polyglycosides of formula (1) or (4) are prepared from syrups of reducing sugars derived from high-hemicellulose plant raw materials or from products or co-products of agricultural origin.

3. The product according to claim 2 wherein the polyglycosides of formula (1) or (4) are prepared from syrups of reducing sugars derived from products or co-products of maize (bran, fibres, and husks of maize), barley (bran) or co-products of wheat (bran and straw) or co-products of wood containing pentoses.

4. The product according to claim 1, characterised in that R1, R2, R3 and R4 are identical and contain 16 to 18 carbon atoms.

5. The product according to claim 1, wherein the emulsifying composition contains 5 to 95% by weight of the mixture of alkyl glycosides of formula (1).

6. The product according to claim 1, wherein the emulsifying composition contains 5 to 75% by weight of the mixture of alcohol esters of formula (2).

7. The product according to claim 1, wherein the emulsifying composition contains 4 to 80% by weight of the alcohol of formula (3).

8. The product of claim 1, characterized in that it comprises the electrolyte in an amount of 20 to 90% by weight.

9. A cosmetic, pharmaceutical or dermopharmaceutical product comprising an emulsifying composition and a paraffin oil, wherein the emulsifying composition is characterized in that it contains by weight, excluding impurities:
   1 to 98% by weight of a mixture of alkyl glycosides of formula (1)

$$R1O(G1)g_1(G2)g_2(G3)g_3(G4)g_4(G5)g_5 \qquad (1)$$

in which:
   R1 is a hydrocarbon radical, linear or branched, saturated or unsaturated, having 10 to 22 carbon atoms,
   G1, G2, G3, G4, G5 are identical or different residues of -oses selected from glucose, galactose, mannose, fructose, ribose, xylose and arabinose
   $g_1, g_2, g_3, g_4$ and $g_5$ being equal to 0 or 1, the sum of $g_1, g_2, g_3, g_4$ and $g_5$ being at least equal to 1
   1 to 90% by weight of a mixture of alcohol esters of formula (2)

$$R2OZ \qquad (2)$$

in which:
   R2 is a hydrocarbon radical, linear or branched, saturated or unsaturated, having 4 to 22 carbon atoms, which can optionally be identical to R1
   Z is then a radical of formula —(CO)(CH2)$_2$(CO)OM obtained by esterification of succinic acid by R2OH in which M is H, Na, K, NH$_4$, [HO(CH2)2]3NH, R2
   1 to 90% by weight of an alcohol of formula (3), $$R3OH \qquad (3)$$

in which:
   R3 is a hydrocarbon radical, linear or branched, saturated or unsaturated, having 10 to 22 carbon atoms, which can optionally be identical to R1 and/or R2
   and 4 to 90% by weight of a mixture of alkyl glycoside esters of formula (4)

$$R4O(X1)x_1(Z)z_1(X2)x_2(Z)z_2(X3)x_3(Z)z_3(X4)x_4(Z)z_4(X5)x_5(Z)z_5 \qquad (4)$$

in which:
- R4 is a hydrocarbon radical, linear or branched, saturated or unsaturated, having 10 to 22 carbon atoms, which can optionally be identical to R1, R2 or R3
- X1, X2, X3, X4, X5 are identical or different residues of oses selected from ribose, xylose and arabinose
- $x_1, x_2, x_3, x_4$ and $x_5$ being equal to 0 or 1, the sum of $x_1, x_2, x_3, x_4$ and $x_5$ being at least equal to 1
- Z is then a radical of formula —(CO)(CH2)$_2$(CO)OM obtained by esterification of succinic acid by a free hydroxyl of X1, X2, X3, X4 or X5, in which M is H, Na, K, NH$_4$, [HO(CH2)2]3NH, R1, R2, R3, R4
- $z_1, z_2, z_3, z_4, z_5$ being equal to 0, 1, 2, 3 or 4, the sum of $z_1, z_2, z_3, z_4, z_5$ being at least equal to 1;
- wherein said product is characterised in that it contains at least 0.1% by weight, relative to the total weight of the product, of the emulsifying composition;
- further wherein said product comprises 10 to 25% by weight.

10. The product according to claim 9, characterised in that the alkyl polyglycosides of formula (1) or (4) are prepared from syrups of reducing sugars derived from high-hemicellulose plant raw materials or from products or co-products of agricultural origin.

11. The product according to claim 9, characterised in that R1, R2, R3 and R4 are identical and contain 16 to 18 carbon atoms.

12. The product according to claim 9, wherein the emulsifying composition contains 5 to 95% by weight of the mixture of alkyl glycosides of formula (1).

13. The product according to claim 9, wherein the emulsifying composition contains 5 to 75% by weight of the mixture of alcohol esters of formula (2).

14. The product according to claim 9, wherein the emulsifying composition contains 4 to 80% by weight of the alcohol of formula (3).

* * * * *